United States Patent [19]

Guttenplan et al.

[11] 4,191,920
[45] Mar. 4, 1980

[54] INSTRUMENT FOR DETECTING CONTAMINATION ON METALLIC SURFACES BY MEASURING SURFACE POTENTIAL DIFFERENCES

[75] Inventors: Jack D. Guttenplan, Santa Ana; Herbert W. Yancey, Downey, both of Calif.

[73] Assignee: Rockwell International Corporation, El Segundo, Calif.

[21] Appl. No.: 842,022

[22] Filed: Oct. 14, 1977

[51] Int. Cl.² ............................................. G01N 27/66
[52] U.S. Cl. ................................ 324/459; 324/71 R
[58] Field of Search ............................... 324/33, 71 R

[56] References Cited

U.S. PATENT DOCUMENTS

| | | | |
|---|---|---|---|
| 2,954,474 | 9/1960 | Lawrance | 324/33 |
| 4,006,063 | 2/1977 | Ensanian | 324/71 |

*Primary Examiner*—Rudolph V. Rolinec
*Assistant Examiner*—Walter Snow
*Attorney, Agent, or Firm*—H. Fredrick Hamann; Gilbert H. Friedman

[57] ABSTRACT

Instrument for the non-destructive detection of contamination on the surface of a metallic object. A reference electrode contains sufficient radioactive material to ionize the air in a gap between the electrode and the metallic object. A buffer amplifier has its input terminals connected to sense the surface potential difference between the electrode and the metallic object. The air gap is typically from one to ten millimeters wide. The input circuit of the buffer amplifier has a resistance very much larger than that of the air gap when the air is ionized. The buffer amplifier drives an alarm device or a display device. A single voltage pick-up is conveniently embodied in a portable hand-held probe. A plurality of voltage pick-ups is incorporated into an array for simultaneously making multiple measurements of surface condition over a large area.

6 Claims, 7 Drawing Figures

INSTRUMENT FOR DETECTING CONTAMINATION ON METALLIC SURFACES BY MEASURING SURFACE POTENTIAL DIFFERENCES

The invention herein was made in the course of or under a contract or sub-contract thereof, with the Air Force.

BACKGROUND OF THE INVENTION

1. Field of the Invention

This invention relates to the determination of the surface condition of a body, and particularly to apparatus for determining the relative freedom from contamination of the surface of a metallic object. The present invention is useful not only in the testing of metals, including alloys, but may also be used with metalloids like germanium, carbon, silicon, boron or the like to determine their surface characteristics. For convenience in reference, the term "metallic" is used herein to include both metals and metalloids.

2. Description of the Prior Art

Contamination of surfaces of metallic parts is a serious problem in, for example, the manufacture of electronic components and electronic systems. Contamination on the surfaces of metallic contacts, for example, may cause considerable difficulty, such as intermittent continuity or even open circuits, and yet this contamination may not be detectable even when the contacts are viewed under a microscope. The bonding of parts to each other by the use of adhesives or by thermocompression techniques, for example, may be adequately strong initially but the bond may deteriorate under normal atmospheric conditions within a few weeks. This deterioration is apparently due to the penetration of moisture into the bonded joints along paths where the bond is weak. Weak bonding is often caused by the prior contamination of the surfaces.

Moisture also penetrates beneath poorly bonded conformal coatings on metallic objects. The moisture tends to concentrate in regions where there is ionic contamination due, for example, to residues of flux from soldering. Eventually the moisture may provide paths for electrical leakage currents and short circuits. In addition, the coatings may develop blisters. Similarly, penetration by moisture often causes metallic platings to blister.

The cost of implementing the controls necessary to achieve adequate surface cleanliness for those steps in the manufacture of, for example, electronic components has had a major impact on overall manufacturing costs in the electronics industry. The present invention represents the results of an effort to reduce such costs through the use of relatively inexpensive and non-destructive test instruments for monitoring surface cleanliness or surface condition. These instruments are suitable for use in on-line quality control procedures in manufacturing.

Surface potential difference (also known as contact potential difference) has been the object of considerable research. The principles involved are well documented in the literature.

Alexander Volta discovered in 1797 that two dissimilar metals placed in contact directly or by means of an intermediate conductor become charged with electricity of opposite polarity. A. Volta, Gehler's Worterbuch, IV, 616 (1801). Since that time, it has been established that the contact potential differences between metals of the same temperature are intrinsic properties of the metals although the measured potential difference is much altered from the intrinsic value by any intervening films on the metals. K. W. Bewig, C. O. Timmons, and W. A. Zisman, "Changes in Contact Potentials of Metals Caused by Adsorbed Monolayers," NRL Report 6200, Feb. 12, 1965. Theoretical research on the relation of contact potential differences to the electronic nature of metallic conductors and to the surface equilibrium of the electrons and ions in each metal lattice were reviewed in C. Herring and M. H. Nichols, *Rev. Modern Phys.*, 21, 185 (1949). The use of contact potentials and the related work function of metals in the study of adsorption, and especially chemisorption, was reviewed in R. Suhrmann, "Changes in Conductivity on Adsorption of Gases on Metal Films," in "Chemisorption," W. E. Gardner, editor, London, Butterworths, p. 106, 1957 and in R. V. Culver and F. C. Tompkins, "Surface Potentials and Adsorption Process on Metals," in "Advances in Catalysts," Vol. XI, New York, Academic Press, p. 67, 1959. There is given in I. F. Patai and M. A. Pomerantz, *J. Franklin Inst.*, 252, 239 (1951) a review of various techniques and apparatus for measuring the contact potential differences between metals. The apparatus discussed there includes various configurations of elements using the ionization method wherein a radioactive source is disposed on one of a pair of metallic electrodes or in the vicinity thereof to ionize the air between the electrodes and thereby "connect" them through a resistive path in the air. The potential difference between the electrodes so connected is measured by an electrometer.

3. Prior Art Statement

The most pertinent prior art discovered by Applicants relative to this invention is listed herewith.

(1) Muchnick, "Ascertaining Surface Condition," U.S. Pat. No. 3,009,100 issued Nov. 14, 1961.

(2) Ensanian, "Method for Measuring Surface Characteristics of Metals and Metalloids," U.S. Pat. No. 4,006,063 issued Feb. 1, 1977.

(3) Smith, *Advan. Colloid Interface Sci.*, 3, 161 (1972)

(4) Guttenplan, "Evaluation of Surface Cleanliness by Surface Potentials"; unpublished paper presented orally at Second Seminar on Contamination: Its Effect, Detection and Control, Anaheim, Calif., Oct. 8–9, 1975.

(5) Hampel, C. A. ed., *The Encyclopedia of Electrochemistry*, pp. 236–239, Reinhold Publishing Corp., New York, 1964.

The patent to Muchnick discloses a method for determining the surface condition of a metallic body. The metallic body is incorporated into an electric circuit. An element or probe is moved close to the body but spaced apart therefrom to define an air gap. A unidirectional source voltage connected between the body and probe is varied to increase the voltage until the air in the gap is ionized and dielectric breakdown occurs. The voltage across the air gap just prior to breakdown is a measure of the condition of the surface of the metallic body. As an alternative to varying the voltage, the air gap can be narrowed until breakdown occurs at a suitable fixed voltage. The spacing at which breakdown occurs is then the measure of surface condition.

The patent to Ensanian discloses a method of mapping the surface condition of a metallic test specimen by measuring the mechanogalvanic potential between successive points on the surface of the specimen and a test probe or standard electrode. The probe is electrically connected to the specimen through a voltage measuring device. The circuit is completed through spaced apart droplets of an electrolyte sprinkled on the surface of the specimen. The electrolyte is a solution of a metallic salt. Alternatively, the circuit is completed through a rotatable non-metallic body of gelled electrolyte mounted on the test probe. One such probe or an array of such probes mounted to a common bracket may be rolled over the surface of the test specimen to map the variations in mechanogalvanic potential. The method of Ensanian is a destructive one in that the testing itself leaves a contaminating residue on the surface of the test specimen and thereby destroys the original character of the surface.

The article by Smith is a study of "Monomolecular Films on Mercury". The elaborate apparatus used for the study includes a reference electrode positioned about 0.5 cm above the surface of a body of mercury in a chamber. The electrode has a small amount of americium of mass number 241 sealed behind a stainless steel foil. The radioactive americium ionized helium cover gas which fills the chamber above the mercury. The surface potential of this arrangement is measured by a very high-impedance electrometer connected between the electrode and the mercury.

In the paper by Guttenplan, apparatus similar to that of Smith is disclosed with the difference that the reference electrode is mounted on a movable base having a three-point support. The height of the electrode relative to the base is adjustable. The paper discloses plans to incorporate such an electrode into a portable instrument having miniaturized electronic components therein for simply, inexpensively, and quickly providing qualitative measures of surface cleanliness. A plan to use such an instrument for controlling a production cleaning process is mentioned.

The encyclopedia entry shows a gas space formed by two plates with surfaces facing each other. The gas is ionized with a weak radioactive source, e.g., polonium 210. As long as there is a contact potential difference between the plates, a field exists between the surfaces and an ionic current flows through the space causing current detectable by a microammeter.

SUMMARY OF THE INVENTION

The general purpose of this invention is to provide a readily useable instrument for the rapid and non-destructive determination of the surface cleanliness of metallic objects or test specimens. The subject invention senses surface potential difference, or contact potential, across a gap of ionized air between a reference electrode having radioactive material incorporated therin and the metallic test specimen. To attain this purpose, the present invention combines miniature electronic components for sensing, amplifying, and converting signals representing surface potential difference. Devices for providing a visible or audible indication of sensed surface conditions are included in the housing of a probe suitable for hand-held use by a human operator. The probe includes a voltage pick-up comprising a reference electrode and means for making electrical contact with a test specimen. Such a probe may be moved about by the operator to scan the condition or relatively large or spaced-apart surfaces. In an alternative embodiment of the invention, a plurality of voltage pick-ups are mounted in a fixed spaced-apart relationship with respect to each other forming an array of pick-ups for an instrument conveniently suitable for making a plurality of simultaneous measurements of the condition of a larger surface. Continuous mapping or monitoring of surface conditions may be accomplished.

DESCRIPTION OF THE PREFERRED EMBODIMENTS

Figure 1:
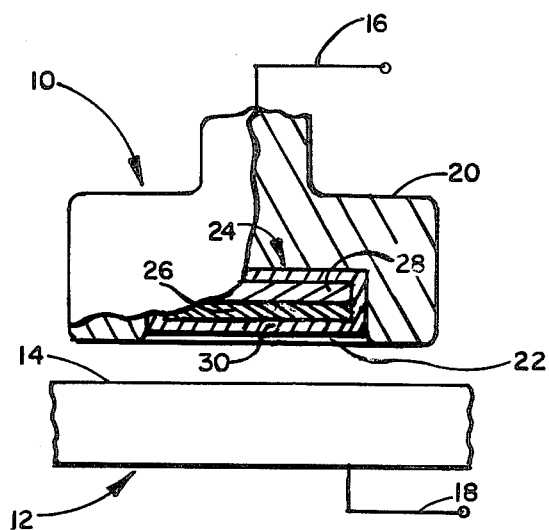
FIG. 1 is a fragmentary sectional view of a prior art reference electrode disposed to measure surface potential difference.

Referring now to FIG. 1, there is shown a prior art reference electrode 10 suitable for use in the measurement of surface potential difference. Reference electrode 10 and its disposition close to, but spaced apart from, surface 14 of metallic object 12 are representative of the prior art approach to the detection of contamination on surface 14. Conductor 16, connected to reference electrode 10, and conductor 18, connected to metallic object 12, are, in turn, connected to the input terminals of an electrometer (not shown) for the measurement of the potential difference between the reference electrode 10 and metallic object 12.

Reference electrode 10 typically has a stainless steel body 20 having a well 22 in the bottom thereof. Well 22 is adapted to receive and hold a capsule 24 containing a radioactive material such as, for example, americium of mass number 241. The capsule 24 typically comprises a layer 26 of the radioactive material on a carrier such as, for example, a layer 28 of silver. The radioactive material and its carrier are sealed in the interior of the capsule 24 by a cover 30 of, for example, gold plating.

Alpha particles from the radioactive material penetrate the cover 30 and ionize the air in the gap between reference electrode 10 and metallic object 12. The width of the air gap is, typically, from about one millimeter to about ten millimeters. When the air is ionized, such an air gap has a resistance of from about $10^{10}$ ohms to about $10^{11}$ ohms. For measurement of voltage independent of air gap resistance, it is well known that the input impedance of the electrometer must be much greater than the resistance of the air gap. An input impedance for the electrometer at least three orders of magnitude greater than that of the air gap, or about $10^{14}$ ohms, is preferred.

Figure 2:
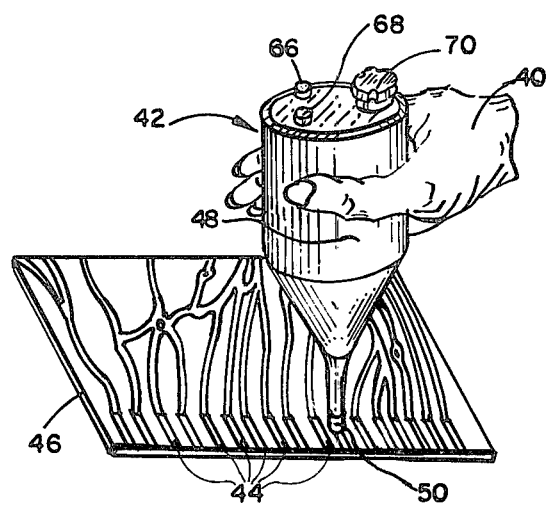
FIG. 2 is a sketch, in perspective, of an instrument in accordance with the subject invention being used to measure surface contamination.

FIG. 2 shows a hand 40 of a human operator holding a probe 42 adapted for conveniently detecting the presence of contamination on metallic surfaces in accordance with the subject invention. The operator is using the probe 42 to inspect the contact fingers 44 of a printed circuit board 46. Shown on the lowest part of a housing 48 for the probe 42 is a ring 50 of metal adapted for making electrical contact with the metallic object being inspected. The ring 50 is directly connected to that portion of the circuitry internal to the housing 48 which is at the potential of the common return circuit (for example, ground) for the instrument. FIG. 2 will be discussed further hereinafter.

Figure 3:
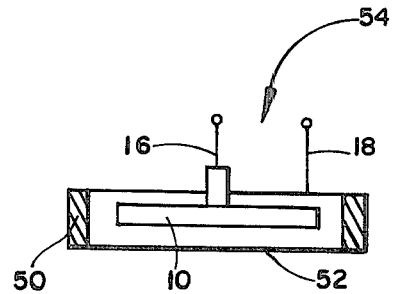
FIG. 3 is a sketch, partly in cross-section, of a detail of the instrument of FIG. 2.

FIG. 3 shows a detail of the probe 42. A reference electrode 10, as in FIG. 1, is shown disposed inside the ring 50 and spaced a suitable fixed distance apart form the bottom rim 52 thereof. As has been indicated, this distance is preferably in the range from about one millimeter to about ten millimeters. As in the embodiment of FIG. 1, conductors 16 and 18, attached to the electrode 10 and ring 50, respectively, are the conductors between which surface potential difference is measured and sensed for further processing. The combination of at least one reference electrode 10 with means for making electrical contact with a test specimen such as ring 50 is termed a voltage pick-up 54.

Figure 4:
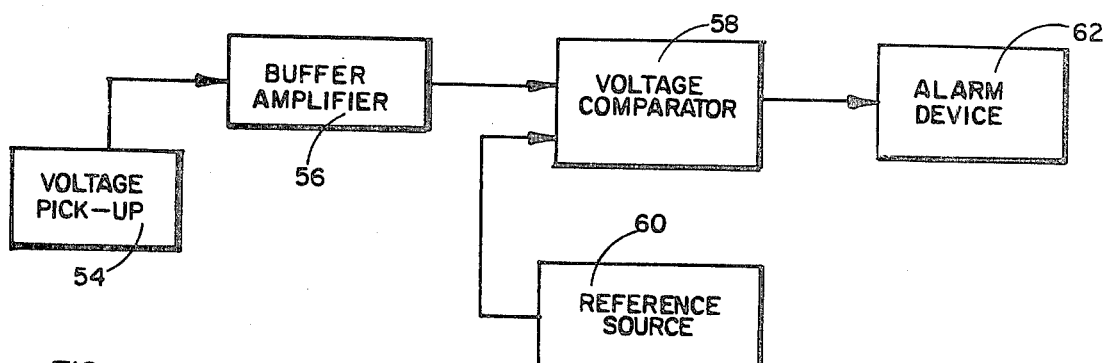
FIG. 4 is a block diagram showing the functional parts of the instrument of FIG. 2.

FIG. 4 shows a functional block diagram for the active electrical and electronic elements of a probe such as the probe 42 of FIG. 2. The surface potential difference sensed by a voltage pick-up 54, such as the one shown in FIG. 3, is applied to the input terminals of a buffer amplifier 56 which may be, for example, an operational amplifier. As with the electrometer of the prior art, the buffer amplifier 56 preferably has an input impedance about three orders of magnitude greater than the resistance of an ionized gap having a width in the range from about one to about ten millimeters. The output signal of the buffer amplifier 56 is one of two input signals applied to voltage comparator 58. The other input signal to voltage comparator 58 is provided by reference source 60. Reference source 60 provides a calibration signal to voltage comparator 58 whereby a threshold voltage for the indication of a contaminated surface is determined. The surface potential difference, as measured by voltage pick-up 54 on a certain contaminated surface, will vary from that measured on the same surface clean by a predetermined variation or threshold. Voltage reference 60 is adjusted to cause the output of voltage comparator 58 to remain in a first state until the surface potential difference measured by voltage pick-up 54 varies from that measured on a clean standard reference surface by the threshold. For greater potential difference variations, the output of voltage comparator 58 switches to a second state. These variations are ordinarily measured in the tens or hundreds of millivolts.

The output signal provided by voltage comparator 58 controls an alarm 62 which, for example, may be activated as the voltage comparator 58 switches from its first state to its second state. As one alternative, the alarm 62 may be a device such as a buzzer for producing an audible signal. As another alternative, the alarm 62 may be a light source such as a lamp, a light emitting diode or the like for producing a visible signal. The visible signal may be a steady glow or a flashing one. As yet another alternative, two differently colored light sources may be provided, one activated when voltage comparator 58 is in its first state for indicating an acceptably clean surface and the other activated when voltage comparator 58 is in its second state to indicate a contaminated surface. Any suitable type of alarm or display may be utilized.

Also required from the functioning of the instrument just described is a power supply which may be, for example, dry cell batteries connected to provide electrical power to each of the functional elements of the instrument in the usual manner.

As will be apparent to those skilled in the art, the functional elements shown in FIG. 4, and described in connection therewith, may all be implemented as miniature parts using, for example, solid state integrated circuitry. Referring again to FIG. 2, it is apparent that those miniature parts, including dry cell batteries for a power supply, may be fitted readily into the housing 48 of the probe 42 and mounted therein for portable hand-held operation of the instrument.

Mounted at the top of the housing 48 shown in FIG. 2, is a pair of light sources 66 and 68 which may be, for example, light emitting diodes. One light source 66 of a first color, e.g., green, may be activated for indicating clean surfaces and the other light source 68 of a second color, e.g., red, may be activated for indicating the presence of contamination on test surfaces.

Also shown at the top of housing 46 is a control knob 70 for a potentiometer (not shown) or any similar device included as part of reference source 60 which may be adjusted to determine a threshold at which the voltage comparator 58 of FIG. 4 changes state as discussed above.

Figure 5:
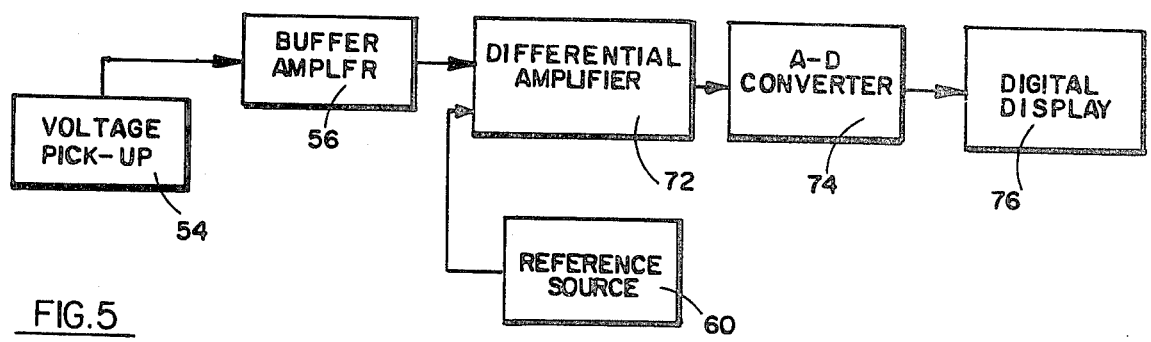
FIG. 5 is a block diagram showing the functional parts of an alternative embodiment of the invention.

FIG. 5 illustrates the functioning of an alternative embodiment of the invention wherein the value of the surface potential difference measured by voltage pick-up 54 is presented to the view of an operator by a digital display 76 such as a segmented numerical display of the type using light emitting diodes or liquid crystals. This display may be mounted, for example, on the top of a housing such as the housing 48 of FIG. 2 in place of the light sources 66 and 68.

For this alternative embodiment, FIG. 5 shows that the output signal of buffer amplifier 56 provides one of the input signals for a differential amplifier 72. The output signal of differential amplifier 72 is a linear function of the output signal of buffer amplifier 56. Reference source 60 provides a second signal to the input of differential amplifier 72 for calibrating the instrument. An adjustment device such as the potentiometer (not shown) adjusted by control knob 70 of FIG. 2, as mentioned above, is used in conjunction with reference source 60 to cause the output of digital display 76 to conform to a standardized value characteristic of the clean metal when voltage pick-up 54 is on a standard reference having a controlled surface characteristic.

Interposed between differential amplifier 72 and digital display 76 is an analog-to-digital converter 74 which functions to convert the output signal of differential amplifier 72 to signals having the proper format for driving digital display 76. As will be apparent to those skilled in the art, the instrument described in connection with FIG. 5 is also capable of being fabricated for use in a portable hand-held probe similar to the probe 42 depicted in FIG. 2. In addition, the availability of the signal in digital format makes the instrument readily adaptable to automated, non-destructive testing and inspection as, for example, on a production line.

Figure 6:
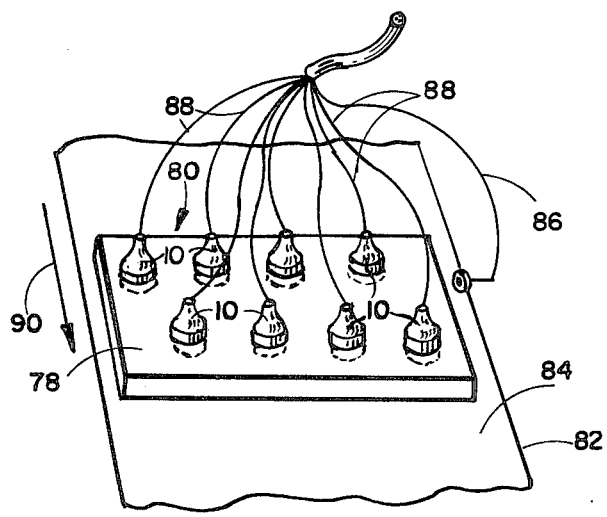
FIG. 6 is a perspective view of an array of reference electrodes mounted in fixed relationship with respect to each other.

FIG. 6 shows a mounting member 78 of insulating material adapted to hold a plurality of reference electrodes 10 in a fixed, spaced-apart, and staggered relationship with respect to each other and in a spaced-apart relationship with respect to a relatively large surface 84 of a metallic object 82. A common conductor lead 86 making electrical contact with metallic object 82 and the conductor leads 88, each attached to one of the reference electrodes 10, form a plurality of voltage pick-up leads for an array 80 of voltage pick-ups 54. The array 80 of voltage pick-ups 54 is adapted to measure a plurality of surface potential differences simultaneously over relatively larger surfaces than can be conveniently examined using a single hand-held probe such as has been described hereinabove. These measurements may be monitored individually or they can be processed to provide, for example, an average measurement.

Each reference electrode 10 is held by mounting member 78 at substantially the same distance, preferably from one to ten millimeters, above the surface 84 of metallic object 82.

Metallic object 82 may be held stationary while its surface 84 is being examined for contamination. In this case, it may be convenient to sweep mounting member 78 over the surface 84 for taking measurements of surface condition over a wide area.

Alternatively, if metallic object 82 is fabricated in the form of a web being moved in the direction, for example, of the arrow 90, mounting member 78 may hold the array 80 fixed in place for making continuous readings.

Each surface potential difference signal provided by each voltage pick-up 54 in the array 80 may be processed to activate an alarm in a manner similar to that discussed in connection with FIG. 4. Alternatively, each of these signals may be processed to drive a digital display in a manner similar to that discussed in connection with FIG. 5.

Figure 7:
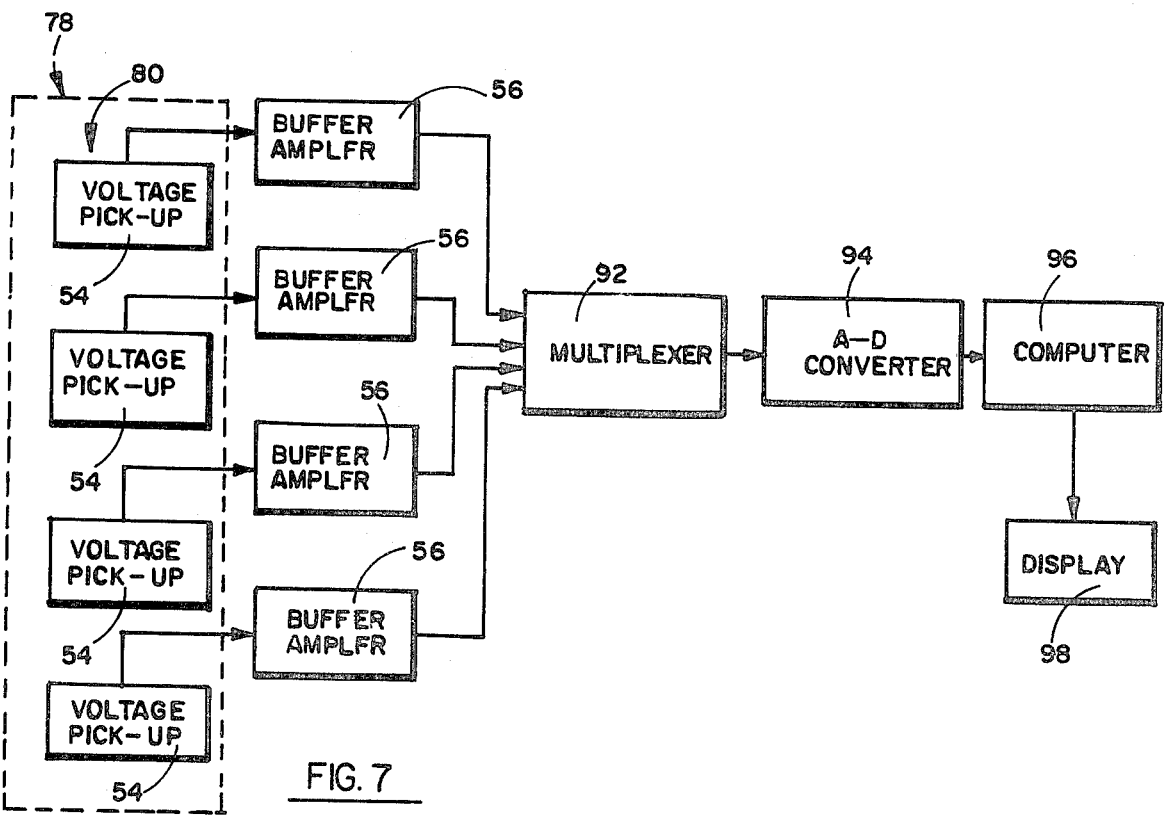
FIG. 7 is a block diagram showing the functional parts of an instrument in accordance with the invention adapted for use with the array of FIG. 6.

Still another alternative embodiment of the invention particularly well suited for use with an array 80 of voltage pick-ups 54 is shown in FIG. 7. The output voltage of each voltage pick-up 54 in the array 80 is applied to the input circuit of a high input impedance buffer amplifier 56. The output signals of the plurality of the buffer amplifiers 56 are connected to the input circuit of a multiplexer 92 which allows samples of all of the signals to be processed sequentially for successive time intervals by the same subsequently used equipment. Analog-to-digital converter 94 converts each signal in each time interval to an equivalent digital number which is then input to computer 96 which may be a microcomputer. As has been suggested, the computer 96 may be used to control the operation of one or more alarm devices or one or more numerical display devices. However, in the preferred embodiment for this alternative to the invention, the computer is used to control the operation of a display 98 such as, for example, a cathode ray tube adapted for displaying numerical information or a printer. The display 98 is preferably controlled to present information to a viewer geometrically arranged in correspondence with the spatial distribution of the respective voltage pick-ups 54 in the array 80. In FIG. 7, the mounting member 78 determining this spatial relationship is represented by dashed box 78 shown surrounding the voltage pick-ups 54 of the array 80.

The computer 96 is also used to calibrate the several voltage pick-ups 54. This is accomplished by placing the array 80 on a standard reference surface having known characteristics. The computer then operates a program which computes and stores a correction value to be applied to the reading given by each of the voltage pick-ups 54. By this method, the measurement made by each voltage pick-up in the array 80 is standarized and harmonized with that of each other voltage pick-up 54.

As will be apparent, the computer may also be used to process the measured data to provide, for example, average measurements. Furthermore, the computer may be readily used to adapt the instrument for use in automated, non-destructive testing and monitoring on a production line.

While the invention has been shown and described with reference to certain preferred embodiments thereof, it will be understood by those skilled in the art that various changes in details may be made therein without departing from the spirit and scope of the invention as set out in the following claims.

Having thus described a preferred embodiment of the invention, what is claimed is:

1. An instrument for sensing surface potential difference, comprising:
   reference electrode means adapted for disposal adjacent to a surface of a metallic object whereby an air gap between said electrode and said surface is defined;
   radioactive means for directing radiation into said air gap wherein said radioactive means is disposed within said electrode so as to ionize the air in said air gap;
   means for making electrical contact directly with said metallic object;
   buffer amplifier means for sensing and amplifying a potential difference between said reference electrode means and said means for making electrical contact;
   said buffer amplifier means having an input circuit impedance sufficiently greater than the resistance of said air gap when said air gap is within predetermined limits of width and when the air in said air gap is ionized by said radiation so that said potential difference is substantially independent of the resistance of said air gap;
   reference means for providing a selectable calibration signal level for the indication of contamination on said surface of said metallic object;
   signal comparison means responsive to said potential difference and said calibration signal for providing a comparison signal signifying contamination on said surface;
   housing means for supporting said reference electrode, for supporting said means for making electrical contact and for enclosing therein said buffer amplifier means and said signal comparison means;
   indicating means responsive to said comparison signal for indicating the presence of contamination on said surface wherein said indicating means is so mounted on said housing means as to be viewable by a human operator; and
   wherein said instrument is formed as a portable probe suitable for hand-held use by said human operator.

2. An instrument as recited in claim 1 wherein said indicating means comprises an alarm device.

3. An instrument as recited in claim 2 wherein said alarm device produces an audible signal.

4. An instrument as recited in claim 2 wherein said alarm device produces a visible signal.

5. An instrument as recited in claim 1 wherein said indicating means comprises a numerical display device.

6. An instrument as recited in claim 5 comprising analog-to-digital converter means interposed between said signal comparison means and said numerical display device for converting said comparison signal from an analog quantity to signals having a proper digital format for driving said numerical display device.

* * * * *